United States Patent
Shytle et al.

(10) Patent No.: US 10,188,613 B2
(45) Date of Patent: *Jan. 29, 2019

(54) EXO-S-MECAMYLAMINE FORMULATION AND USE IN TREATMENT

(71) Applicant: UNIVERSITY OF SOUTH FLORIDA, Tampa, FL (US)

(72) Inventors: Douglas Shytle, Largo, FL (US); Paul R. Sanberg, Spring Hill, FL (US); Mary Newman, Valrico, FL (US); Archie A. Silver, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/970,656

(22) Filed: May 3, 2018

(65) Prior Publication Data

US 2018/0250244 A1  Sep. 6, 2018

Related U.S. Application Data

(63) Continuation of application No. 15/456,934, filed on Mar. 13, 2017, now abandoned, which is a continuation of application No. 14/205,721, filed on Mar. 12, 2014, now Pat. No. 9,593,070, which is a continuation of application No. 12/886,887, filed on Sep. 21, 2010, now abandoned, which is a continuation of application No. 12/651,813, filed on Jan. 4, 2010, now Pat. No. 8,026,283, which is a continuation of application No. 11/278,770, filed on Apr. 5, 2006, now abandoned, which is a continuation of application No. 10/441,947, filed on May 19, 2003, now Pat. No. 7,101,916, which is a continuation of application No. 09/882,935, filed on Jun. 15, 2001, now Pat. No. 6,734,215, which is a continuation-in-part of application No. PCT/US99/30153, filed on Dec. 16, 1999.

(60) Provisional application No. 60/112,534, filed on Dec. 16, 1998.

(51) Int. Cl.
*A61K 31/13* (2006.01)
*C07C 211/38* (2006.01)
*A61K 9/00* (2006.01)

(52) U.S. Cl.
CPC ............ *A61K 31/13* (2013.01); *A61K 9/0019* (2013.01); *C07C 211/38* (2013.01)

(58) Field of Classification Search
None
See application file for complete search history.

(56) References Cited

U.S. PATENT DOCUMENTS

| | | | |
|---|---|---|---|
| 4,749,686 A | 6/1988 | Hintze | |
| 5,039,801 A | 8/1991 | Brossi et al. | |
| 5,686,448 A | 11/1997 | Baldone | |
| 5,986,142 A | 11/1999 | Magni et al. | |
| 6,034,079 A | 3/2000 | Sanberg et al. | |
| 6,121,289 A | 9/2000 | Houdi | |
| 6,197,827 B1 | 3/2001 | Cary | |
| 6,734,215 B2 | 5/2004 | Shytle et al. | |
| 7,101,916 B2 | 9/2006 | Shytle et al. | |
| 8,026,283 B2 | 9/2011 | Shytle et al. | |
| 9,593,070 B2 | 3/2017 | Shytle et al. | |

OTHER PUBLICATIONS

Suchocki, et al. "Synthesis of 2-exo- and 2-endo-Mecamylamine Analogues. Structure-Activity Relationships for Nicotinic Antagonism in the Central Nervous System" *Journal of Medicinal Chemistry*, 1991, pp. 1003-1010, vol. 34.
Solomons, *Organic Chemistry*, 3rd Ed., 1984, p. 419.
Stone, C. A. et al. "Chemistry and Structure-Activity Relationships of Mecamylamine and Derivatives" *Journal of Medicinal and Pharmaceutical Chemistry*, 1962, pp. 665-690, vol. 5, No. 4.
Martin, T. J. et al. "Pharmacological Evaluation of the Antagonism of Nicotine's Central Effects by Mecamylamine and Pempidine" *The Journal for Pharmacology and Experimental Therapeutics*, 1990, pp. 45-51, vol. 254, No. 1.
Braddom, R. L. et al. "Autonomic Dysreflexia: A Survey of Current Treatment" *American Journal of Physical Medicine and Rehabilitation*, Oct. 1991, pp. 234-241, vol. 70, No. 5, Abstract only.
MedlinePlus, "Chronic Fatigue Syndrome", downloaded on Oct. 26, 2017, retrieved from the Internet, URL: www.medlineplus.gov/chronicfatiguesyndrome.html, pp. 1-4.

(Continued)

*Primary Examiner* — Savitha M Rao
*Assistant Examiner* — Gregg Polansky
(74) *Attorney, Agent, or Firm* — Saliwanchik, Lloyd & Eisenschenk

(57) ABSTRACT

A pharmaceutical composition includes a therapeutically effective amount of exo-S-mecamylamine or a pharmaceutically acceptable salt thereof, substantially free of exo-R-mecamylamine in combination with a pharmaceutically acceptable carrier. Preferably the amount is about 0.5 mg to about 20 mg. Medical conditions are treated by administering a therapeutically effective amount of exo-S-mecamylamine or a pharmaceutically acceptable salt thereof, substantially free of its exo-R-mecamylamine, said amount being sufficient to ameliorate the medical condition. The medical conditions include but are not limited to substance addiction (involving nicotine, cocaine, alcohol, amphetamine, opiate, other psychostimulant and a combination thereof), aiding smoking cessation, treating weight gain associated with smoking cessation, hypertension, hypertensive crisis, Tourette's Syndrome and other tremors, cancer (such as small cell lung cancer), atherogenic profile, neuropsychiatric disorders (such as bipolar disorder, depressoin, an anxiety disorder, schizophrenia, a seizure disorder, Parkinson's disease and attention deficit hyperactivity disorder), chronic fatigue syndrome, Crohn's disease, autonomic dysreflexia, and spasmogenic intestinal disorders.

11 Claims, 5 Drawing Sheets

(56) References Cited

OTHER PUBLICATIONS

Howard, G. et al. "Cigarette Smoking and Progression of Atherosclerosis" *JAMA*, Jan. 14, 1996, pp. 119-124, vol. 279, No. 2.
Smirk, F. H. et al. "Use of Mecamylamine in the Management of Hypertension" *British Medical Journal*, Feb. 23, 1957, pp. 422-425, vol. 1(5016).
Tennant, F. S. et al. "Clinical Evaluation of Mecamylamine for Withdrawal From Nicotine Dependence" *NIDA Research Monograph Series*, Mar. 1984, pp. 1-11, vol. 49.
Breuer-Katschinski, B. D. et al. "Effect of cigarette smoking on the course of Crohn's disease" *European Journal of Gastroenterology and Hepatology*, Mar. 1996, p. 1, vol. 8, No. 3, Abstract only.

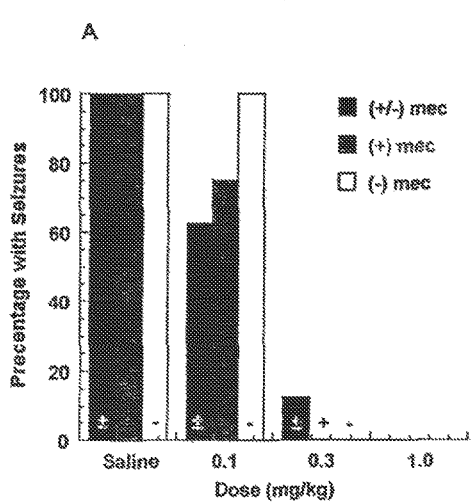
Figure 6-A
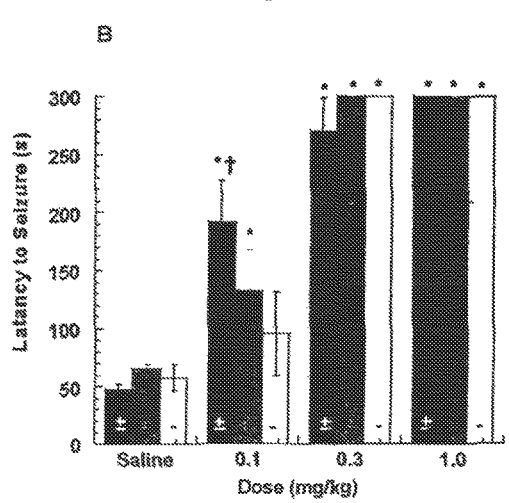
Figure 6-B
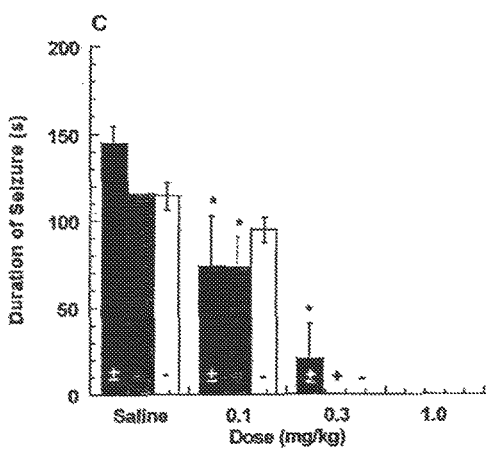
Figure 6-C
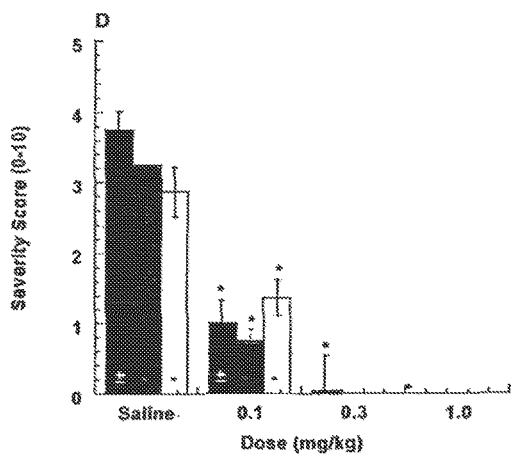
Figure 6-D

EXO-S-MECAMYLAMINE FORMULATION AND USE IN TREATMENT

CROSS-REFERENCE TO RELATED APPLICATIONS

This application is a continuation of Ser. No. 15/456,934, filed Mar. 13, 2017, which is a continuation of Ser. No. 14/205,721, filed Mar. 12, 2014, now U.S. Pat. No. 9,593,070, which is a continuation of Ser. No. 12/886,887, filed Sep. 21, 2010, abandoned, which is a continuation of Ser. No. 12/651,813, filed Jan. 4, 2010, now U.S. Pat. No. 8,026,283, which is a continuation of Ser. No. 11/278,770, filed Apr. 5, 2006, abandoned, which is a continuation of Ser. No. 10/441,947, filed May 19, 2003, now U.S. Pat. No. 7,101,916, which is a continuation of Ser. No. 09/882,935, filed Jun. 15, 2001, now U.S. Pat. No. 6,734,215, which is a continuation-in-part of PCT/US99/30153, filed Dec. 16, 1999, which claims the benefit of U.S. Provisional Application No. 60/112,534, filed Dec. 16, 1998.

BACKGROUND (1) Field of the Invention

The present invention is in the field of chemical synthesis of stereoisomers and more particularly the exo-S-mecamylamine stereoisomer and the use of exo-S-mecamylamine in medical treatments.

(2) Description of Related Art

Mecamylamine (N,2,3,3-tetramethylbicyclo-[2.1.1]heptan-2-amine hydrochloride, 826-39-1) was developed and characterized by Merck & Co., Inc., as a ganglionic blocker with clinically significant hypotensive actions (Stone et al., J Med Pharm Chem 5(4):665-90, 1962). Unique characteristics of mecamylamine—including exceptional oral efficacy, rapid onset, long duration of action, and nearly complete absorption from the gastrointestinal tract—made mecamylamine at that time more desirable than the existing ganglionic blockers (Baer et al., Am J Physiol 186:180-6, 1956).

Despite mecamylamine's proven efficacy in the treatment of hypertension, its side effects resulting from broad parasympathetic inhibition led to its demise as a first line treatment for essential hypertension. Generalized ganglionic blockade may result in atony of the bladder and gastrointestinal tract impaired sexual function, cycloplegia, xerostomia, diminished perspiration and postural hypotension. Among mecamylamine side effects experienced at the antihypertensive dose of 25 mg/day were cardiovascular effects, hypothermia, tremors, anti-diuresis, antinociception, blurred vision, impotency, dysuria, tremor, choreiform movements, mental aberrations, nervousness, depression, anxiety, insomnia, slurred speech, weakness, fatigue, sedation, headache, constipation and renal insufficiency. Even at lower doses, such as 7.5 mg/day, some evidence for constipation has been reported. Minor increases in taste perversion (altered sense of taste), dizziness, insomnia and dyspepsia were noted. Mecamylamine continued to be used in special situations, such as hypertensive encephalopathy (Moser, 1969), hypertensive crises, and autonomic dysreflexia (Braddom and Johnson, 1969; Braddom and Rocco, 1991). Outside of a few laboratories and an occasional clinical study, sales of mecamylamine are rare.

In addition to its peripheral ganglionic blocking actions, mecamylamine crosses the blood brain barrier and functions as a selective nicotinic receptor antagonist at doses which do not have a significant effect on parasympathetic function (Banerjee et al., Biochem Pharmacol 40:2105-10, 1990; Martin et al., Med Chem Res 2:564-77, 1993). As a result, mecamylamine blocks most of the physiological, behavioral, and reinforcing effects of tobacco and nicotine (Martin et al., Biochem Pharmacol 38:3391-7, 1989). In studies of nicotine dependence, doses of 2.5 to 20 mg have been administered acutely to human subjects. For example, Rose et al. (1989) found that low doses of mecamylamine (2.5 to 10 mg), which were well tolerated, reduced the subjective effects of smoking in adult smokers.

In a recent double blind placebo-controlled study investigating the benefits of oral mecamylamine (5 mg/day b.i.d.) in adults for smoking cessation treatment, there was no significant increase over controls in adverse effects reported with mecamylamine treatment for most symptoms, including blurred vision, dizziness when standing, dry mouth, weakness, abdominal pains, or difficult urination. The most prevalent symptom with the mecamylamine treatment was mild constipation; at some point during the five weeks of mecamylamine treatment, 70% of the subjects reported that symptom versus 32% in the placebo group (Rose et al., 1994). Mecamylamine also has been reported to alter cognitive functioning (Newhouse P A et al, Neuropsychopharmacology 10:93-107, 1994), electrical brain waves (Pickworth W B, Herning R I, Henningfield J E, Pharmacology Biochemistry & Behavior 30:149-153, 1988) and cortical blood flow (Gitalman D R, Prohovnik I, Neurobiology of Aging 13:313-318, 1992).

While most animal studies used more than 0.5 mg/kg, Driscoll found that a small dose of only mecamylamine (<0.3 mg/kg, not 0.5 mg/kg) to high-avoidance rats increased their avoidance success almost as much as 0.1 mg/kg nicotine (but less than 0.2 mg/kg nicotine). Based on his experiments, Driscoll concluded: "mecamylamine may exert unpredictable effects on rats at the dosage levels used to block nicotine in behavioral tests" (Driscoll P., Psychopharmacologia (Berl.) 46:119-21, 1976).

Many organic compounds exist in optically active forms, i.e., they have the ability to rotate the plane of polarized light. In describing an optically active compound, the prefixes R and S are used to denote the absolute configuration of the molecule about its chiral center(s). The prefixes (+) and (−) or d and l are employed to designate the sign of rotation of polarized light by the compound, with (−) and l meaning that the compound is levorotatory. A compound prefixed with (+) and d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs are optically active. One example is the l-form of propranolol, which is about 100 times more potent than the d-form. Optical purity is important since certain isomers may be deleterious rather than simply inert. Another example is d-thalidomide that appears to be a safe and effective sedative for controlling morning sickness during pregnancy; whereas, l-thalidomide is thought to be a potent teratogen.

Mecamylamine has been marketed as a racemic mixture comprising the optical isomers exo-S-mecamylamine and exo-R-mecamylamine hydrochloride. Previous studies aimed at investigating the pharmacology of these two isomers have generally found little or no difference in potency or efficacy. For example, Stone et al. (1962) compared the effects of (+)-mecamylamine hydrochloride with racemic mecamylamine hydrochloride on nicotine-induced convulsions and pupil dilation and found essentially no significant differences between the two compounds and concluded that "optical isomerism does not play a significant role in determining the degree of activity." (Stone, supra, p.675). Schonenberger et al. (Helv Chim Acta 69:283-7, 1986) reported "interesting differences" in the actions of d- and l-mecamylamine hydrochloride in assays measuring neuromuscular transmission. However, they provided no details on the differences.

In U.S. Pat. No. 5,039,801, Brossi and Schonenberger disclosed that "the antipodes (−)- and (+)-mecamylamine were obtained here from the corresponding methylbenzylureas in 40% yield each and were of high optical purity (95%, HPLC), affording hydrochloride salts which were optically pure after one crystallization." (col. 3, lines 32-37). However, in disclosing their experimental findings, they mention that the "etheral extract of the concentrated, acidified reaction mixture was concentrated and the residue distilled (Kugel, 180°, 20 torr) to give 6.08 g (96%) (−)-12 as a tlc. pure colorless liquid which turned to a waxy solid on standing in cold: $[\alpha]_D=77.0°$ (c+2.6 in benzene) lit. (+)-12: $[\alpha]_D=+80.1°$ (c=3 in benzene). The combined org extracts from the alkaline aqueous phase were concentrated, the resulting liquid was mixed with 20 ml $Et_2O$ and crude hydrochloride (+)-1.HCl was precipitated by addition of a slight excess of HCl in $Et_2O$. After filtration, the finely powdered colorless solid was recrystallized from 2-propanol to give 1.02 g (64%) (+)-1.HCl as needles $[\alpha]_D+20.1°$ (c+1.7 in $CHCl_3$). The more polar urea 3 (1.85 g, 5.89 mmol) was treated in exactly the same manner to give 752 mg (63%) (−)-1.HCl as colorless needles: $[\alpha]_D-20.0°$ (c=2.2 in $CHCl_3$)." Col. 6, lines 20-37. However, no in vitro or in vivo data were disclosed.

Suchocki et al. (J Med Chem 34:1003-10, 1991) investigated the actions of d- and l-mecamylamine hydrochloride in assays measuring nicotine-induced depression of spontaneous locomotor activity and antinociception. They found that both optical isomers had similar potency in blocking the antinociception caused by nicotine; whereas, the potency of the (+)-mecamylamine isomer in blocking the nicotine-induced depression of spontaneous locomotor activity was unable to be determined due to an experimental confound.

Tourette's Syndrome (TS) is an autosomal dominant neuropsychiatric disorder characterized by a range of symptoms, including multiple motor and phonic tics. It is a hyperkinetic movement disorder expressed largely by sudden, rapid, brief, recurrent, nonrhythmic, stereotyped motor movements (motor tics) or sounds (phonic tics), experienced as irresistible impulses but which can be suppressed for varying lengths of time (Tourette Syndrome Classification Study Group, Arch Neurol 50:1013-16). Motor tics generally include eye blinking, head jerking, shoulder shrugging and facial grimacing, while phonic or vocal tics include throat clearing, sniffling, yelping, tongue clicking and coprolalia. The symptoms typically begin in childhood and range from relatively mild to very severe over the course of a patient's lifetime (Robertson M M, Br J Psychiatry, 154: 147-169, 1989). Many TS patients also exhibit other neuropsychiatric abnormalities including obsessive compulsive symptoms (Pauls D L et al. Psychopharm Bull, 22:730-733, 1986), hyperactivity and attention deficit (Comings Del., Himes J A, Comings B G, J Clin Psychiatry, 51:463-469, 1990). Problems with extreme temper or aggressive behavior also are frequent (Riddle Mass. et al. Wiley Series in Child and Adolescent Mental Health, Eds. Cohen D J, Bruun, R D, Leckman J F, New York City, John Wiley and Sons, pp. 151-162, 1988; Stelf M E, Bornstein R A, Hammond L, A survey of Tourette Syndrome patients and their families: the 1987 Ohio Tourette Survey, Cincinnati, Ohio Tourette Syndrome Association, 1988), as are school refusal and learning disabilities (Harris D, Silver A A, Learning Disabilities, 6(1): 1-7, 1995; Silver A A, Hagin R A, Disorders of Learning Childhood, Noshpitz J D, ed. New York City: Wiley, pp. 469-508, 1990).

While the pathogenesis of TS is still unknown, excessive striatal dopamine and/or dopamine receptor hypersensitivity has been proposed (Singer H S et al. Ann Neurol, 12:361-366, 1982), based largely on the therapeutic effectiveness of dopamine receptor antagonists. TS is frequently treated with the dopamine antagonist haloperidol (Haldol®, Ortho-McNeil Pharmaceutical, Raritan, N.J.), which is effective in about 70% of cases (Erenberg G, Cruse R P, Rothner, A D, Ann Neurol, 22:383-385, 1987; Shapiro A K, Shapiro E, Wiley series in child and adolescent mental health, Eds. Cohen D J, Bruun R D, Leckman J F, New York City, John Wiley and Sons, pp. 267-280, 1988). Other neuroleptics include pimozide (Shapiro E S et al. Arch Gen Psychiatry, 46:722-730, 1989), fluphenazine (Singer H S, Gammon K, Quaskey S. Pediat Neuroscience, 12:71-74, 1985-1986), and risperidone (Stamenkovic et al., Lancet 344:1577-78, 1994). The α-adrenergic agonist clonidine, which also is effective for associated attention deficit hyperactivity disorder (ADHD), has only a 40% success rate for motor and vocal tics (Brunn R D, J Am Acad Child Psychiatry, 23:126-133, 1984; Cohen D J et al. Arch Gen Psychiatry 37:1350-1357, 1980). Other medications with varying degrees of effectiveness include clonazepam (Gonce M, Barbeau A. Can J Neurol Sci 4:279-283, 1977), naloxone (Davidson P W et al. Appl Res Ment Retardation 4:1-4, 1983) and fluoxetine (Riddle M A et al. J Am Acad Child Adol Psychiatry 29:45-48, 1990). A commonly used medication is haloperidol (Erenberg G, Cruse R P, Rothner A D, Ann Neurol, 22:383-385, 1987). However, therapeutic doses of haloperidol frequently cause difficulty in concentration, drowsiness, depression, weight gain, parkinsonian-like symptoms—and with long-term use—tardive dyskenesia (Shapiro A K, Shapiro E, Tourette's Syndrome and Tic Disorders: Clinical Understanding and Treatment. Wiley series in child and adolescent mental health. Eds. Cohen, D J, Bruun, R D, Leckman J F, New York City, John Wiley and Sons, pp. 267-298, 1988). The side effect of tardive dyskinesia is particularly bothersome because it may add additional abnormal, involuntary movements of the tongue, jaw, trunk and/or extremities.

Erenberg et al. (Erenberg G, Cruse R P, Rothner A D, Ann Neurol 22:383-385, 1987) found that most patients with TS stop using their haloperidol or other neuroleptic medications by age 16, often because of side effects. After TS patients quit medication, they have less control over speech and movement, which disqualify many for full-time, responsible jobs. The public, including law enforcement officers, often identify the symptoms as intoxication. Unexpected movements and coprolalia cause great social difficulties.

It has been observed that 50% of children presenting with TS also have Attention Deficit Hyperactivity disorder (ADHD). ADHD is a neurobiological disorder characterized by impaired attentiveness, increased impulsivity, and hyperactivity. ADHD is now the most commonly diagnosed childhood psychiatric condition, with some 3.5 million afflicted. In addition, 60% of adolescents with ADHD continue to have symptoms in adulthood, representing another 2.5 million patients.

Many neuropsychiatric disorders involve abnormal or involuntary movements including but not limited to obsessive-compulsive disorder (OCD), TS, ADHD, hemidystonia, and chorea, such as Huntington's chorea. These diseases may be caused by neurochemical imbalances in the brain's basal ganglia. Acetylcholine, by activating nAChrs in the basal ganglia, regulates motor activity in humans (Clarke PBS, Pert A, Brain Res 348:355-358, 1985). Nicotinic stimulation excites activity in the dopamine (DA)-producing cells in the basal ganglia (Clarke PBS et al, J Pharmacol Exper Therapeutics 246:701-708, 1988; Grenhoff J, Aston-Jones G, Svennson T H, Acta Physiol Scand 128:351-358, 1986; Imperato A, Mulas A, Di Chiara G, Eur J Pharmacol 132:337-338, 1986), while mecamylamine blocks nAChr and inhibits DA release from basal ganglia structures (Ahtee L, Kaakkola S, Br J Pharmacol 62:213-218, 1978).

U.S. Pat. No. 5,574,052 to Rose and Levin discloses agonist-antagonist combinations to reduce the use of nicotine and other drugs. In combination with nicotine, the nicotinic antagonist mecamylamine was given to treat tobacco dependency. Rose and Levin proposed including both nicotine and mecamylamine in a patch. Rose and Levin also suggested that such agonist-antagonist combinations could be used in other psychopathological disorders and cases involving neuronal dysfunction (e.g., manic depression, schizophrenia and hypertension due to sympathetic autonomic disorder).

It would benefit patients to be able to have better symptom control and fewer side effects. Our clinical experience with mecamylamine racemate in human patients with a variety of disorders supports a variety of uses. Herein is disclosed improved symptom control with isomer exo-S-mecamylamine for the treatment of a variety of nicotine-responsive neuropsychiatric disorders.

SUMMARY OF THE INVENTION

It is an object of the present invention to provide improved therapy for patients with nicotine-responsive neuropsychiatric disorders.

It is a further object of the present invention to provide therapy with fewer side effects to improve patient medication compliance, as well as to improve their quality of life and social functioning.

In one embodiment, there is provided a pharmaceutical composition that includes a therapeutically effective amount of exo-S-mecamylamine or a pharmaceutically acceptable salt thereof, substantially free of exo-R-mecamylamine in combination with a pharmaceutically acceptable carrier. Preferably the amount is about 0.5 mg to about 1000 mg. The preferred composition contains exo-S-mecamylamine hydrochloride and a pharmaceutically acceptable carrier. The pharmaceutical composition of claim 1 can be adapted for oral, intrathecal, transdermal, implantable and/or intravenous administration. The pharmaceutical can be a transdermal patch, solid preparation, or a sustained release form. Preferably, the substantially pure exo-S-mecamylamine is greater than 95% by weight and exo-R-mecamylamine is less than 5% by weight. More preferably, the substantially pure exo-S-mecamylamine is greater than 98% by weight and exo-R-mecamylamine is less than 2% by weight. More preferably, the substantially pure exo-S-mecamylamine is greater than greater than 99% by weight and exo-R-mecamylamine is less than 1% by weight. Even more preferably, the substantially pure exo-S-mecamylamine is greater than 99.5% by weight and exo-R-mecamylamine is less than 0.5% by weight. Most preferably, the substantially pure exo-s-mecamylamine is greater than 99.7% by weight and exo-R-mecamylamine is less than 0.3% by weight.

In other embodiments, there are provided treatments of medical conditions by administering a therapeutically effective amount of exo-S-mecamylamine or a pharmaceutically acceptable salt thereof, substantially free of its exo-R-mecamylamine, said amount being sufficient to ameliorate the medical condition. Preferably, the method provides for administering exo-S-mecamylamine intravenously, intramuscularly, transdermally, intrathecally, orally or by bolus injection. Preferably, the dosage of exo-S-mecamylamine is about 0.5 mg to about 1000 mg, depending on dosage form and its expected life. Preferably, exo-S-mecamylamine is administered one to four times per day. The medical conditions include but are not limited to substance addiction (involving nicotine, cocaine, alcohol, amphetamine, opiate, other psychostimulant and a combination thereof), aiding smoking cessation, treating weight gain associated with smoking cessation, hypertension, hypertensive crisis, herpes type I and II, Tourette's Syndrome and other tremors, cancer (such as small cell lung cancer), atherogenic profile, neuropsychiatric disorders (such as bipolar disorder, depression, anxiety disorder, panic disorder, schizophrenia, seizure disorders, Parkinson's disease and attention deficit hyperactivity disorder), chronic fatigue syndrome, Crohn's disease, autonomic dysreflexia, and spasmogenic intestinal disorders.

BRIEF DESCRIPTION OF THE DRAWING(S)

Figure 3:
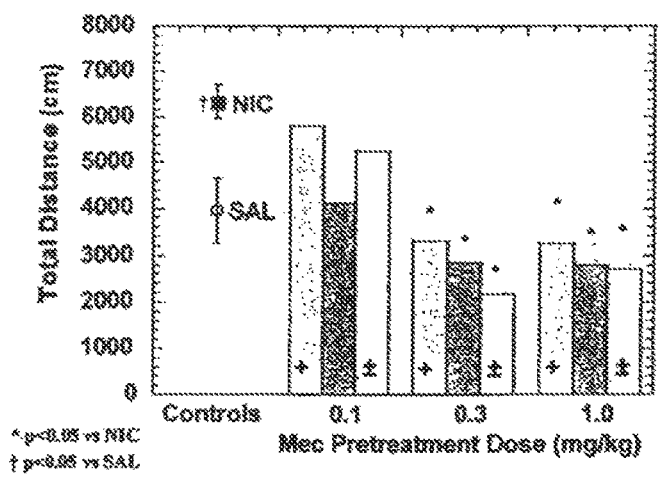

FIG. 3 is a bar graph showing total distance traveled in 60 minutes by rats having undergone seven days of sensitization with saline or mecamylamine at one of 3 doses. The dagger symbol indicates significant differences from the Saline/Saline control group. The asterisk identifies significant differences from the Saline/Nicotine control group.

Figure 4:
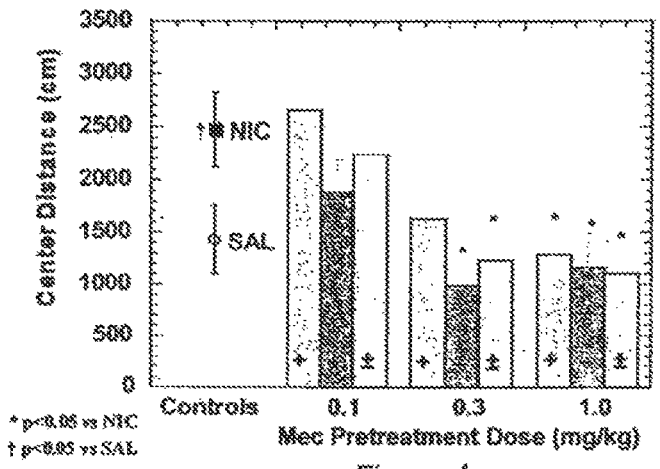

FIG. 4 is a bar graph showing the center distance traveled by rats in the same study.

Figure 5:
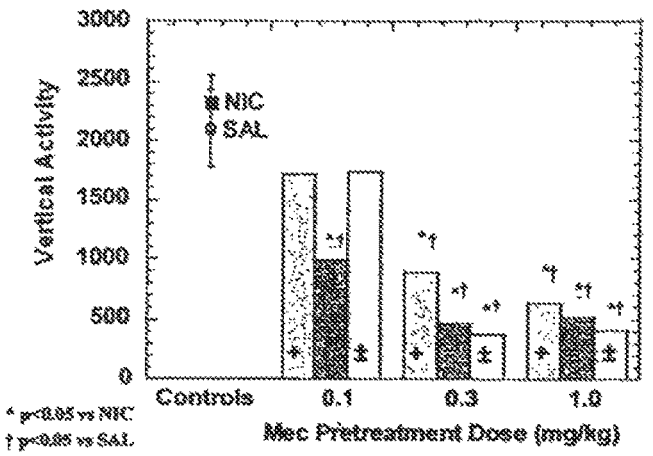

FIG. 5 is a bar graph showing the vertical activity of rats in the same study.

FIGS. 6A-6D are bar graphs showing the percentage of rats that seized (6A), latency to seizure (6B), duration of seizure (6C), and severity of seizures in rats treated with saline or various doses of mecamylamine and its stereoisomers followed by nicotine (3.6 mg/kg).

Figure 7:
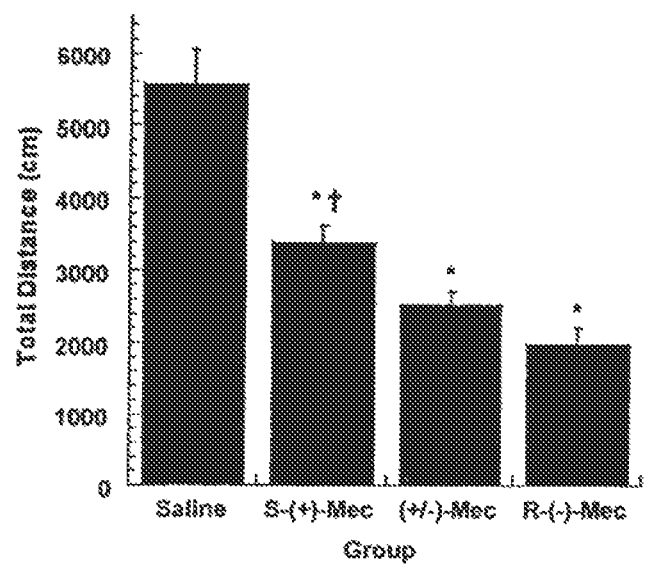

FIG. 7 is a bar graph illustrating the mean total distance traveled in centimeters in rats receiving any of saline or 10 mg/kg mecamylamine or its stereoisomer.

DETAILED DESCRIPTION OF THE INVENTION

Although there is some variability from one patient to another, it is generally observed that, by administering an effective amount of only exo-S-mecamylamine, it is possible to accomplish a more "targeted" therapy, which provides the desired effect without the consequences of all the other pharmacologic effects. This is important since it is not desirable for all patients to be administered a compound with such a multifaceted spectrum of activity.

Synthesis of mecamylamine has been disclosed in three patents: U.S. Pat. No. 2,831,027 (1958), U.S. Pat. No. 2,885,428 (1959) and U.S. Pat. No. 5,986,142 (1999).

For the synthesis of mecamylamine one starting material is camphene, the racemate or either isomer. The isomers are available from natural sources or can be obtained by resolution using liquid chromatography using a chiral medium (Armstrong, J Chrom A, 666:445, 1994). They can also be made using kinetic resolution wherein a chiral reagent selectively reacts with one isomer leaving the other intact (Jenke, J Organomet Chem, 405:383, 1991). The camphene isomers can also be made from chiral precursors (Hana, Chem Ber, 111:2527, 1978).

Camphene, racemic or isomeric, in an acidic medium can be reacted with a nitrogen source, such as azide (Pancrazi, Bull Chim Soc (Fr.), (1977) 162), cyanide (Stein, J Am Chem Soc, 78:1514, 1956; Stone, J Med Pharm Chem, 5:665, 1962; Pfister, U.S. Pat. No. 2,831,027 (1958)) or thiocyanate (Luskin, U.S. Pat. No. 2,885,428; CA. 53:20124h). The intermediates so produced can be converted to mecamylamine, the racemate or either isomer.

Camphene, racemic or isomeric, can be converted to camphene hydrochloride (Geam, Aust J Chem, 27:567, 1974) which can be reacted with nitrite (Huckel, Ann 528 (1937) 57; CA. 31:3033-4) to produce an intermediate which can be converted to mecamylamine, the racemate or either isomer. The hydrochloride can also be reacted with an amine to yield mecamylamine, racemic or isomeric (Stone, J Med Pharm Chem, 5:665, 1962), or an intermediate that can be converted to mecamylamine, racemic or either isomer.

Camphenilone, racemic or as either of its isomers, can be reacted with a methyl lithium or similar nucleophilic methyl to give an alcohol (Stone, J Med Pharm Chem, 5:665, 1962; Gream, Aust J Chem, 27 (1974) 567). The alcohol or its derivatives can be subjected to the acidic reactions described above for camphene to yield mecamylamine, racemic or as either of its isomers, or products that can be converted to it (Stone, J Med Pharm Chem 5:665, 1962). A similar alcohol can be made from camphene, racemic or isomeric (Coxon, Tetrahedron, 26:3755, 1970) and subjected to the same reactions yielding similar products.

The reaction of organic azides with camphene, racemic or as either of its isomers followed by either photolytic or thermal decomposition (Huisgen, Chem Ber, 98:3992, 1965; Franz, J Org Chem, 29:2922, 1964) of the reaction product yields an aziridine which can be ring opened (Gold, J Org Chem, 37:2208, 1972) and transformed into mecamylamine, the racemate or either isomer.

Mecamylamine can be synthesized in either the racemic form or the isomers. The racemic product can be resolved into its isomers by salt formation using chiral acids (carboxylic, sulphonic, phosphoric (Pfister, U.S. Pat. No. 2,831,027 (1958); Stone, J Med Pharm Chem, 5:665, 1962) and then the isomer regenerated, by derivatization with chiral molecules. The resulting diastereomers can be separated by crystallization or by simple chromatography (Schonenberger, Helv. Chim. Acta., 69 (1986) 283), and then the stereoisomer regenerated, or by liquid chromatography using a chiral medium.

Definitions:

"exo-S-Mecamylamine" includes the +-stereoisomer of N,2,3,3-tetramethylbicyclo-[2.1.1]heptan-2-amine hydrochloride, 826-39-1. This stereoisomer is also referred to as exo-S-N,2,3,3-tetramethyl-bicycl-o-[2.1.1]heptan-2-amine hydrochloride. It has positive optical rotation. "exo-R-mecamylamine" is the (−)-stereoisomer.

"Related exo-S-mecamylamine compounds" include various active stereoisomers and substituted analogs of mecamylamine (Stone et al., J Med Pharm Chem 5(4):665-90, 1962, hereby incorporated by reference). Activity can be tested in rats by nicotine convulsions, pupil dilatation and by other methods such as those described below. Such activity was routinely lost with larger substitutions for the methyl groups, which are not a part of this invention. Both methyl or dimethyl groups on the amino group were more active than other substituents and are included herein. The d form was active; however, the dl racemate appeared to be slightly more active. Consequently the l form seems to have significant activity. Stone et al. reported that the exo form (methylamino group lies on the same plane as the methylene bridge) was always stronger than the endo form (methylamino group lies below the methylene bridge and tends to lie within the cage created by the bridge). In addition, a partial structure, 2,2,-dimethyl-3-methylaminobutane, also was active. Stone concluded that the slight differences in activity between different models for the d form and other analogs was not significant.

The term "substantially free of the exo-R-mecamylamine hydrochloride" as used herein means that the composition contains at least about 95% by weight of exo-S-mecamylamine and less than about 5% by weight of exo-R-mecamylamine. In a more preferred embodiment, the composition contains at least 98% by weight of exo-S-mecamylamine and less than about 2% by weight of exo-R-mecamylamine. In the most preferred embodiment, the composition contains at least 99% by weight of exo-S-mecamylamine and less than about 1% by weight of exo-R-mecamylamine.

"Beneficial effect" is a noticeable improvement over the baseline clinically observable signs and symptoms and may include subjective patient reports of improvement. For example, a beneficial effect in motor disorders includes decreases in tic frequency or severity, but improvements also can be manifested indirectly through reductions in anxiety, aggressive outbursts, and premonitory urges that often precede or compound the severity of abnormal movements. Treatment effects can be quantified by clinical observations and videotape scoring. Beneficial effects can also be predicted by the results of animal screening. For example, Suemaru et al (ibid) has proposed that the nicotine-induced rat-tail tremor can be used to screen for compounds to treat tremors. Repeated nicotine administration can induce locomotor hyperactivity and a tail tremor in rats which is blocked with mecamylamine (0.1-1 mg/day, ip) but not by hexamethonium which does not readily enter the brain. (Suemaru K., Oishi R, Gomita Y, Arch Pharm 350:153-57, 1994).

The Yale Global Tic Severity Scale (YGTTS) is the most widely used clinical assessment rating scale used to assess tic symptoms. It provides an objective measure of tic frequency of severity based on clinical observations. This scale includes a tic symptom inventory, which is filled out based on the patient's personal recall of tics occurring over the previous week. Using this inventory as a guide, the clinician then rates the severity of both motor and vocal tics on five separate dimensions: number, frequency, intensity, complexity, and interference. In addition, there is also a separate rating of global impairment, which characterizes the impact of the disorder on the patient's social function, self-esteem, etc., over the previous week. There are numerous rating systems that can be substituted therefore.

An objective method for rating tic symptoms employs video recording of patients. A videotape of at least five minutes is viewed and the frequency and severity of both motor and vocal tics are recorded. Video taping has proven a valuable adjunct to clinical rating systems for drug trials (Leckman J F, et al., Arch Gen Psychiatry, 48:324-328, 1991; Shapiro E S, et al., Arch Gen Psychiatry, 46:722-730, 1989; McConville B J, Fogelson M H, Norman A B, Klykylo W M, Manderscheid M A, Parker K W, Sanberg P R, Am J Psychiatry, 148:793-794, 1991; Silver A A, Shytle R D, Philipp M K, Sanberg P R, The Effects of Nicotine on Biological Systems II. PBS Clarke, M. Quik and K. Thurau, (Eds.); Advances in Pharmacological Sciences, Birkhauser Publishers, pp. 293-299, 1995; Reveley M A, et al., Journal of Psychopharmacology Supplement, A30, 117, 1994).

Beneficial effects in obsessive compulsive disorders include diminution in the obsessive or compulsive behavior, which can be confirmed by patient or family reports or psychiatric assessment. Beneficial effects in nicotine, alcohol or cocaine abuse include longer drug-free periods as well as subjective feelings of less need for the drug. Beneficial effects in herpes infections include aborting outbreaks, faster healing and longer infection-free period.

"Side effects" are unwanted actions which may include but are not limited to cardiovascular effects, hypothermia, tremors, anti-diuresis, antinociception, blurred vision, impotency, dysuria, tremor, choreiform movements, mental aberrations, nervousness, depression, anxiety, insomnia, slurred speech, weakness, fatigue, sedation, headache, constipation, renal insufficiency, taste perversion (altered sense of taste), dizziness, and dyspepsia.

The term "effective amount" refers to the amount of exo-S-mecamylamine that is necessary to provide benefit. The precise amount required will vary depending upon the age and weight of the subject, severity of the disorder, route of administration, and so forth, but may easily be determined by routine experimentation, as described below in the clinical examples. In general, however, an effective amount of exo-S-mecamylamine range from about 0.001 mg/kg to about 6 mg/kg per day, preferably about 0.002 mg/kg to about 3 mg/kg, more preferably about 0.005 mg/kg to about 2 mg/kg, and most preferably about 0.01 to about 1.5 mg/kg. A starting dose for adults with drug-resistant TS is about 2.5 mg per day, with dosage adjusted according to return of symptoms. A small child with mild ADHD preferably starts with 1 mg per day or less.

The term "pharmaceutically acceptable" refers to a lack of unacceptable toxicity in a compound, such as a salt or excipient. Pharmaceutically acceptable salts combine inorganic anions such as chloride, bromide, iodide, sulfate, sulfite, nitrate, nitrite, phosphate, and the like, and organic anions such as acetate, malonate, pyruvate, propionate, cinnamate, tosylate, mesylate, citrate, and the like Pharmaceutically acceptable excipients are described at length by E. W. Martin, in Remington's Pharmaceutical Sciences (Mack Publishing Co.).

Pharmaceutical compositions containing exo-S-mecamylamine may contain one or more pharmaceutical carriers. The term "pharmaceutically acceptable carrier" refers to any generally acceptable excipient that is relatively inert, non-toxic and non-irritating. When the carrier serves as a diluent, it may be solid, semisolid, or liquid material acting as a vehicle, excipient, or medium for the active ingredient. Pharmaceutical unit dosage forms may be prepared for administration by any of several routes, including, but not limited to, oral and parenteral (especially by intramuscular and intravenous injection, or by intrathecal, subcutaneous implant or transdermal administration). Representative of such forms are tablets, soft and hard gelatin capsules, powders, lozenges, chewing gums, emulsions, suspensions, syrups, solutions, sterile injectable solutions, and sterile packaged powders. Compositions containing nicotine antagonists may be formulated by procedures known in the art so as to provide rapid, sustained, or delayed release of any or all of the compounds after administration. In addition to the common dosage forms set out above, the compounds of the present invention may also be administered by controlled release means and/or delivery devices such as those described in U.S. Pat. Nos. 3,845,770; 3,916,899; 3,536,809; 3,598,123; 4,008,719; 5,910,321; 5,348,746; and the like by the various manufacturers of controlled release means and/or delivery devices.

As the exo-S-mecamylamine formulation of the present invention is well suited to oral administration, preferred carriers facilitate formulation in tablet or capsule form. Solid pharmaceutical excipients such as magnesium stearate, calcium carbonate, silica, starch, sucrose, dextrose, polyethylene glycol (PEG), talc, and the like may be used with other conventional pharmaceutical adjuvants including fillers, lubricants, wetting agents, preserving agents, disintegrating agents, flavoring agents, and binders such as gelatin, gum arabic, cellulose, methylcellulose, and the like, to form admixtures which may be used as such or may be tabulated, encapsulated, or prepared in other suitable forms as noted above. A general description of formulation is given in Remington's Pharmaceutical Sciences (Mack Publishing Co.).

Modes of Administration

Administration is preferably by oral dosage but may be by transdermal application, intranasal spray, bronchial inhalation, suppository, parenteral injection (e.g., intramuscular or intravenous injection), and the like. Carriers for parenteral administration include, without limitation, aqueous solutions of dextrose, mannitol, mannose, sorbitol, saline and other electrolyte solutions, pure water, ethanol, glycerol, propylene glycol, peanut oil, sesame oil, polyoxyethylene-polyoxypropylene block polymers, and the like. One may additionally include suitable preservatives, stabilizers, antioxidants, antimicrobials and buffering agents, for example, BHA, BHT, citric acid, ascorbic acid, tetracycline, and the like. Alternatively, one may incorporate or encapsulate the nicotine antagonist formulation in a suitable polymer matrix or membrane, thus providing a sustained-release delivery device suitable for implantation or application to the skin. Other devices include indwelling catheters and devices such as the Alzet® minipump.

The invention has been disclosed by direct description. The following are examples showing the efficacy of the method in providing benefit. The examples are only examples and should not be taken in any way as limiting to the scope of the method.

Analysis of exo-S-Mecamylamine Hydrochloride

Figure 1:
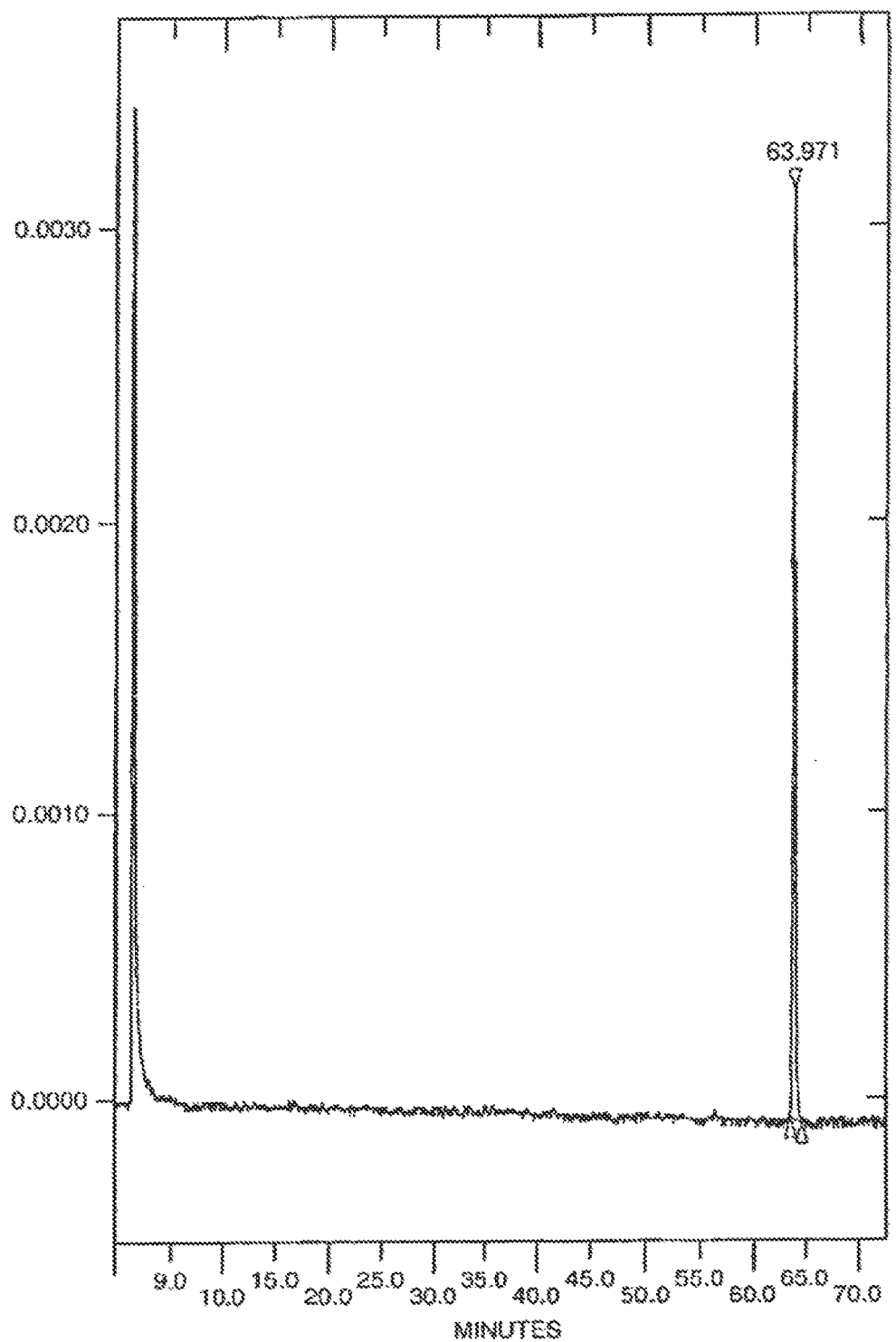
FIG. 1 is a gas chromatograph printout showing that exo-S-mecamylamine elutes purely at 63.971 minutes after placement on the column.
Figure 2:
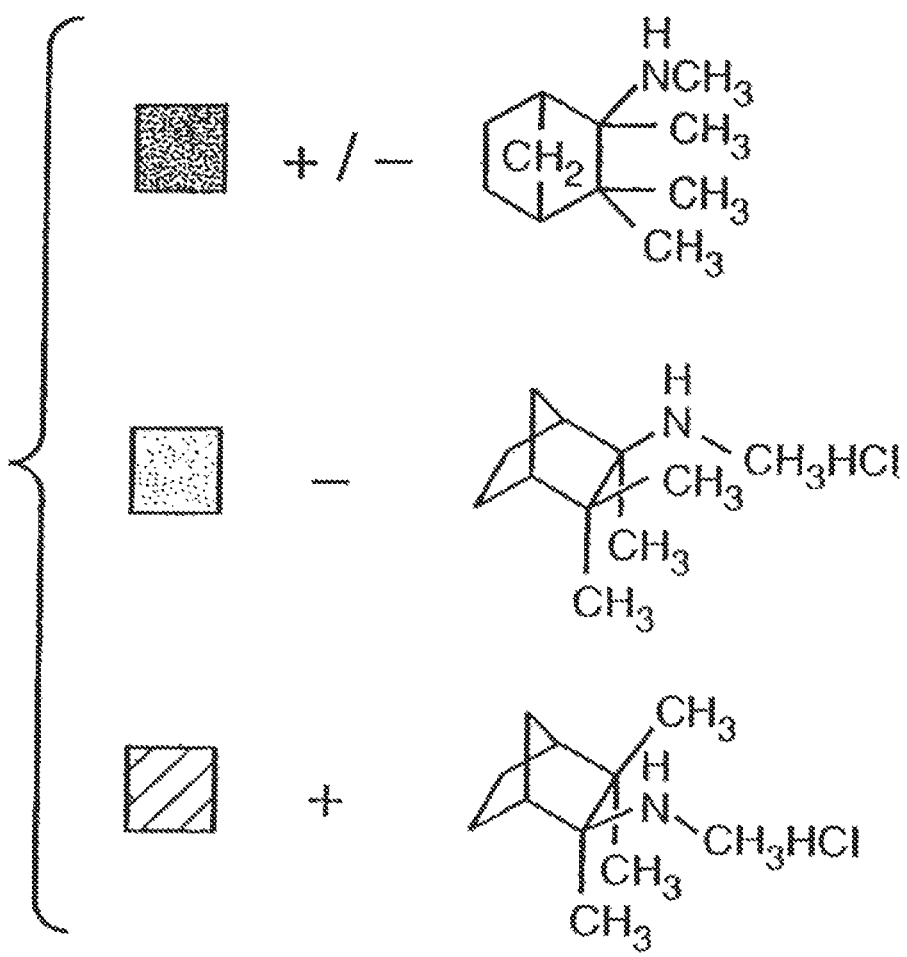
FIG. 2 shows the structures of mecamylamine generally (+/−).

Mecamylamine hydrochloride (Lot 2351) was 99.95% pure by gas chromatograph, as shown in FIG. 1. The gas chromatograph retained exo-S-mecamylamine hydrochloride for 63.971 minutes, and no other significant peaks were observed. The chloride content was 17.2%. Considering that chloride comprises 17.4% of the mass of mecamylamine hydrochloride, this indicates a high level of purity. No camphene or other impurities were detected. Optical rotation was +19.4°. This lot was used in Examples 1 and 9 below. The structures of mecamylamine and the stereoisomers are shown in FIG. 2.

Pharmacology
General Methods
Animals

Male Sprague-Dawley rats (Zici-Miller Laboratories, Allison Park, Pa.) weighing an average of 463 grams were used. They were housed in groups of 2-4 per cage, allowed free access to food and water, and maintained on a reverse 12 h light/12 h dark lighting cycle, with night being 8:00 AM through 8:00 PM. All testing occurred during the rats' nocturnal cycle.

Measurements and Apparatus

For all locomotor testing, a Digiscan Animal Activity Monitors (Model RXYSCM, Accusan, Inc., Columbus, Ohio) was used. Box dimensions were 42 cm×42 cm×30 cm, and the walls and floors were clear acrylic. Each box used in this study had photocells that, when the light beam was broken by the rat's movement, calculate a number of variables. All locomotor activity was automatically captured and recorded with a Digipro software program.

To assess catalepsy (the ability to maintain position after being placed therein) induced by haloperidol and blocked with treatment, the bar test was used. The bar was placed 9 cm above the tabletop. The rat's forepaws were simultaneously placed on the bar and the hind paws placed under the rat for support. Time was measured from the second both forepaws were placed on the bar until the rat removed both paws from the bar. The minimum time was 1 second, and the maximum time allowed was 60 seconds. The shorter the time on the bar, the greater the blockage of haloperidol-induced catalepsy.

Drugs

Mecamylamine HCl was obtained from Layton Bioscience, Inc., Atherton, Calif. Optical isomers of mecamylamine were resolved from the racemate according to procedures reported by Stone et al (supra), but with significant modifications to improve optical purity and yields (see above). (−)-Nicotine was obtained from Sigma Chemical Co. (St. Louis, Mo.). Haloperidol lactate (Solopak®) was obtained from a local pharmacy. All drugs were dissolved in saline at a volume of 1 mg/ml and injected subcutaneously.

EXAMPLE 1

Eighty-eight experimentally naive adult male Sprague-Dawley derived rats were housed two per cage and allowed free access to food and water. Each rat received a randomly assigned pretreatment condition for seven consecutive days. On each day of this pretreatment period, rats received an injection of saline, racemic mecamylamine, exo-R-mecamylamine, or exo-S-mecamylamine 20 minutes prior to receiving a second injection of either saline or nicotine (0.4 mg/kg s.c.) and left in their home cage. Pretreatment assignment was arranged so that 2 rats from each condition were started and tested together to control for sequence effects. Rats received no treatment or testing on the day 8. On day 9, rats were tested for the presence of the sensitized locomotor stimulant response to nicotine. Each rat was placed into a locomotor box for a 60 minute habituation period, followed by an injection of nicotine (0.4 mg/kg s.c.), and then placed immediately back into the locomotor box. A computer recorded data over the next 60 minutes at 5-minute intervals.

FIGS. 3-5 illustrate 3 dependent variables respectively for all groups following a test injection of 0.4 mg/kg nicotine on day 9. The saline/nicotine (sal/nic) pretreatment group exhibited a sensitized locomotor response to nicotine, which was not evident in any of the mecamylamine/nicotine (mec/nic) pretreatment groups. Further post-hoc comparisons indicated that the locomotor response to nicotine was significantly greater for the sal/nic pretreatment group when compared to the other groups (p<0.05). The response to nicotine in the mec/nic pretreatment groups was not significantly different from those receiving no nicotine in the sal/sal pretreatment group (p<0.05), except in the case of vertical activity, where all mec/nic groups had significantly less activity then control.

Pretreatment with mecamylamine and both of its stereoisomers on nicotine exposure days, dose-dependently prevented the development of the sensitized locomotor responses to nicotine. Decreased vertical activity following the test injection of nicotine alone (day 9) was found in rats that had received chronic mecamylamine/nicotine exposure relative to those who had received chronic saline/saline exposure. This suggests that chronic exposure to mecamylamine actually reduce the locomotor response to nicotine to levels below that seen in the saline/saline group. Although both isomers of mecamylamine followed the same general pattern, exo-R-mecamylamine was generally more effective at lower doses, particularly for center distance and vertical activity.

EXAMPLE 2

Recently it has been shown that some seizure disorders, including but not limited to juvenile myoclonic epilepsy, autosomal dominant nocturnal frontal lobe epilepsy and possibly inherited idiopathic epilepsy, are mediated through the $\alpha_4$ and $\alpha_7$ nicotine-binding receptors. Nicotine has been shown to induce short periods of seizure activity in rats. Nicotine may function in two distinct neuropharmacological ways to induce seizures: first, by activation of nAChRs involved with presynaptic glutamate release and second, by causing inactivation of nAChRs involved with presynaptic gamma-amino butyric acid (GAVA) release. Okamoto et al. (Jpn J Pharmacol 59:449-55, 1992) showed that a single high dose of mecamylamine (1.0 mg/kg) blocked nicotine-induced seizures in rats. The present experiment evaluates the effect of exo-R-mecamylamine and exo-S-mecamylamine and the racemate in blocking nicotine-induced seizures in rats. In addition, because $\alpha 4\beta 2$ $\alpha 7$ nAChR antagonists (dihydro-$\beta$-erythroidine and methyllycaconitine, respectively) can also induce seizures, a high dose of mecamylamine and its isomers were also tested alone for potential seizure production.

Methods
Animals

Male Sprague-Dawley rats (n=96) weighing between 200 and 250 grams upon arrival were used for this study (Harlan Laboratories, Ind.). The rats were housed two per cage, allowed one week to acclimate to animal facility before testing, kept on a reverse lighting schedule (7:00-19:00 lights off), and allowed free access to food and water. Testing occurred between 10:00 a.m. and 3:00 p.m. in a dimly lit room maintained at 22° C. The experimental procedures carried out in this study were in compliance with the Guide for the Care and Use of Laboratory Animals (National Research Council, 1996) and had the prior approval of the University of South Florida Institutional Animal Care and Use Committee.

Apparatus

Observation of seizures and locomotor recordings were carried out in clear acrylic 41×41×30 cm test chambers inside Digiscan activity monitors (Accuscan, Inc.). Each monitor employs two arrays of infrared photocell beams (8×8 photocells, model RXYZCM-8) to detect several parameters of the rat's movement both horizontally and vertically. Data were collected in 5-min bins during testing.

Drugs (−) Nicotine was purchased from Sigma Chemical Co., (St. Louis, Mo.) and (+/−)-Mecamylamine hydrochloride (Inversine®) and its stereoisomers was obtained from Layton Bioscience, Inc., Sunnyvale, Calif.). All drugs were dissolved in physiological saline, and nicotine was adjusted to pH with HCl to 7.40. All rats received subcutaneous (s.c.) injections in a volume of 1 ml/kg, and the drugs were prepared fresh each day. All doses are expressed as the free base of the drug.

Mecamylamine Blockade of Nicotine-Induced Seizures

Ninety-six rats were randomly assigned to one of three conditions (n=32 per condition): (±)-mecamylamine, exo-R-mecamylamine, or exo-S-mecamylamine. Rats in each condition were randomly assigned to one of four treatment-drug groups (n=8 per group): 0.0 (saline), 0.1, 0.3, or 1.0 mg/kg mecamylamine. Two rats from each group, per condition, were tested at a time in a counter-balanced design. All testing for a condition was complete in a day. Rats were moved to the behavior observation room 30 minutes prior to testing. They received an injection (s.c.) in their home cages of (±)-mecamylamine, one of its stereoisomers, or saline 15 minutes prior to nicotine injection of 3.6 mg/kg (s.c.). After nicotine injection they were individually placed directly into a test chamber for 30 minutes of observation and locomotor activity recording.

Two experimenters who were blind to the treatment groups of the rats recorded the following measures: number of seizures, latency to seize, and duration of seizure(s). In addition, during the 30-minute testing period, rats were rated once every 5 minutes on a severity scale, which ranged from 0-5. This scale was anchored to the following descriptors: 0=no seizures, 1=myoclonic jerk, 2=forelimb clonus, 3=clonic/tonic seizure, 4=compete tonus (all four limbs), and 5=death. Other secondary measures were also recorded at 5-min intervals on scales from 0-10, with 10 being the most severe, consisting of the following measures: severity of tremors, difficulty breathing, vocalization, activity level, and righting.

Effects of Mecamylamine Alone at High Dose

Thirty-two rats were randomly assigned to 4 groups (n=8 per group) receiving saline or 10 mg/kg (s.c.) of either (±)-mecamylamine, exo-R-mecamylamine, and exo-S-mecamylamine. Immediately following injection, each rat was placed in the test chamber for 30 minutes of observation and locomotor activity recording. Two rats from each group were tested at one time in a counterbalanced design to control for order effects. All testing was completed in one day.

Statistical Analysis

Data was analyzed using a one-way analysis of variance followed by Fishers least significance test for multiple comparisons. Statistical significance was set at an alpha level of 0.05.

Results

Mecamylamine Blockade of Nicotine-Induced Seizures

Nicotine at 3.6 mg/kg produced 100% seizures in all the saline pretreatment groups (FIG. 6A). Mecamylamine and its stereoisomers prevented nicotine-induced seizures in a dose-dependent manner (FIG. 6A). There was a significant overall effect for the measures of seizure latency, duration, and seizure [F(11, 84)=37.24, 19.97, 30.17; p (all) 0.0001, respectively]. Group comparisons on the seizure latency showed that at 0.3 and 1.0 mg/kg (±)-mecamylamine and its stereoisomers had significantly longer latency when compared to their saline control groups and the groups across the 0.1 mg/kg condition. Furthermore, rats in the 0.1 mg/kg for both (±) and exo-S-mecamylamine groups had significantly longer seizure latency than their saline comparison groups. Also, at this dose the (±) mecamylamine showed longer seizure latency when compared to the exo-R-mecamylamine group (FIG. 6B).

On the measures of duration and severity of seizure, rats in (±)-mecamylamine and in the stereoisomers at 0.3 and 1.0 mg/kg groups were significantly different from their saline comparison groups and the other groups. However, in the 0.1 mg/kg treatment condition, the (±)- and exo-S-mecamylamine groups were significantly different from their saline comparison groups, where as rats in the exo-R-mecamylamine group did not differ from their saline comparison group (FIG. 6C).

Even though the rats in 0.1 mg/kg condition had more seizures than rats in both the 0.3 and 1.0 mg/kg condition the severity of seizures were significantly less than that of their saline comparison groups (FIG. 6D). No differences in secondary measures including locomotor activity were found between racemic mecamylamine and its isomers in these experiments (data not shown).

Effects of Mecamylamine Alone at High Dose

There was no evidence for mecamylamine-induced seizures when administered at the high dose of 10 mg/kg (data not shown). However, significant differences in spontaneous locomotor activity were found between isomers of mecamylamine when compared to saline control [F (3,28)=26; p=0.0001]. As represented in FIG. 7, all three mecamylamine compounds reduced spontaneous locomotor activity as measured in total distance traveled, with the exo-S-mecamylamine isomer exhibiting signigicantly less locomotor depressant effects than the exo-R-mecamylamine.

The present study demonstrated that mecamylamine and its optical isomers block nicotine-induced seizures at low doses and that the exo-S-mecamylamine isomer appears to have inhibitory properties more similar to racemic mecamylamine than the exo-R-mecamylamine isomer. For example, fewer rats had nicotine-seizures in the racemic and exo-S-mecamylamine groups than did the exo-R-mecamylamine at the lowest dose (0.1 mg/kg) tested. Moreover, at this dose, only the racemic and exo-S-mecamylamine groups significantly increased seizure latency and decreased the duration of seizures.

When tested alone at a high dose of 10 mg/kg, mecamylamine and its stereoisomers failed to produce seizures. This finding is inconsistent with a recent report of other nAChR antagonists causing seizures when given alone and does not support the hypothesis that nAChR inactivation is one way that nicotine causes seizures.

Another finding of the present study was exo-S-mecamylamine caused significantly less locomotor depressant effects than exo-R-mecamylamine at 10 mg/kg. This result is consistent with the finding that exo-S-mecamylamine has less inhibitory effect at nAChR muscle receptors than exo-R-mecamylamine. Because muscle weakness is a common side effect associated with mecamylamine treatment of children and adolescents, our findings, together with others', have important clinical implications. The fact that exo-S-mecamylamine has inhibitory properties more similar to racemic mecamylamine than to exo-R-mecamylamine, but with less motor depressant effects than either, suggests that exo-S-mecamylamine would be a better medication for clinical development.

There are a few limitations of the present findings that deserve discussion. First, since seizure suppression was virtually complete with 2 of the 3 doses, the doses chosen were too high to permit us to conclude that exo-S-mecamylamine is more potent than exo-R-mecamylamine. Moreover, in the absence of any pharmacokinetic data on the isomers of mecamylamine, we cannot conclude that the differences found between the isomers in the present study are solely due to pharmacodynamic differences in their inhibitory properties at nAChrRs. Nevertheless, the differences that were found were consistent with what would be expected based on the available pharmacological evidence regarding the differences observed at the receptor level.

In summary, mecamylamine and its stereoisomers potently block nicotine-induced seizures in rats with exo-S-mecamylamine displaying an overall higher therapeutic index over exo-R-mecamylamine.

EXAMPLE 3

The aim of the study was to determine whether mecamylamine and its stereoisomers have any effect on pressor responses and increases in plasma catecholamines in response to sympathetic nerve stimulation. As previously established in the model of the pithed rat, modulation of these responses indicates changes in the release of adrenergic neurotransmitters and the responsiveness of the cardiovascular system thereto.

Methods and Study Design

In the vagotomized, pithed and artificially respired rats (with oxygen mixed with air), the cardiovascular responses to test compounds measured were mean arterial blood pressure and heart rate; and the catecholamine responses measured were plasma norepinephrine, epinephrine and dopamine. These variables were measured in rats at rest and after electrical stimulation of sympathetic outflow at 0.2 Hz, 0.8 Hz, and 2.2 Hz for a one-minute duration (50 V, 1 msec pulse), and before and after administration of vehicle or a drug. Catecholamine assays were performed by specific HPLC testing. Four groups of rats were studied: those treated with saline, exo-R-mecamylamine, (+/−)-mecamylamine and exo-S-mecamylamine by bolus injection of 0.1 mg/kg, 1.0 mg/kg, and 10 mg/kg, administered intravenously. Statistical analysis were applied as appropriate.

Results—Cardiovascular Responses

In the vagotomized, pithed and artificially respired rats (with oxygen mixed with air), resting mean blood arterial pressure (MAP) was approximately 48 mmHg and heart rate was approximately 280 beats/min in all groups. In saline-treated rats, sympathetic nerve stimulation increased MAP in a frequency-dependent manner by 4.2±1.0 mmHg at 0.2 Hz, 16.1±4.9 mmHg at 0.8 Hz, and 27.1±7.1 mmHg (or up to around 80 mmHg MAP) at 2.2 Hz (all significantly different from baseline, $p<0.05$). In all other groups, rats treated with exo-R-mecamylamine, exo-S-mecamylamine and the racemate, the stimulation-induced increases in MAP were reduced at all frequencies but were completely abolished at 0.8 and 2.2 Hz ($p<0.05$ compared to saline-treated rats). Of all the drugs, exo-S-mecamylamine was the most potent because it shifted the MAP-stimulation frequency response curve significantly to the right of the one obtained in the presence of saline already at 0.1 mg/kg. The other two forms, exo-R-mecamylamine and the racemate, significantly right-shifted the pressure-stimulation curves at 1.0 and 10 mg/kg doses of the drugs. In each of the drug-treated groups, changes in the MAP from baseline ($\delta$ MAP) during 0.8 Hz and 2.2 Hz were significantly lower than those of the saline-treated rats, and for the highest dose of the drugs, stimulation at these frequencies actually caused the MAP to fall below baseline levels ($p<0.05$).

Heart rate responses to nerve stimulation were also similarly affected by treatment with mecamylamine. At the highest dose of the drug, exo-R-mecamylamine and exo-S-mecamylamine and the racemate all significantly lowered the increases in heart rate ($\delta$ HR) at 2.2 Hz as compared to those obtained in the saline-treated rats ($p<0.05$). As with the pressor responses, stimulation-induced tachycardia was completely blocked at 10 mg/kg of all forms of mecamylamine. There were no differences between the potencies of the three forms of mecamylamine in respect to blocking the tachycardic response. The EC50s for the stimulation-induced pressor responses ($\delta$ MAPs) could not be determined because the maximal pressor responses were not achieved for technical reasons.

Catecholamine Responses

Plasma catecholamine (CA) levels—norepinephrine (NE), epinephrine (EPI), and dopamine (DA)—were measured by HPLC with an electrochemical detector following administration of doses of all forms of mecamylamine.

Resting plasma NE levels were between 100-200 pg/ml in all groups of pithed rats and were not significantly different from each other. The sympatholytic stimulation at 2.2 Hz evoked significant increases in plasma NE levels (increases from baseline and absolute values) in all mecamylamine-treatment groups. However, the stimulation-induced increases in plasma NE levels were significantly less in rats treated with exo-R-mecamylamine than in those in the saline treatment group ($p<0.05$).

Resting plasma EPI levels were between 50-60 pg/ml in all groups of pithed rats and were not significantly different from each other. The sympathetic stimulation at 2.2 Hz evoked increases in plasma EPI levels (from baseline and absolute values) in rats treated with saline and exo-R-mecamylamine ($p<0.05$). However, following the administration of the racemate and exo-S-mecamylamine, there was a significant decrease in stimulation-induced plasma EPI responses at 2.2 Hz as compared to those of the saline-treated rats ($p<0.05$).

Surprising results were found by measuring plasma DA levels in the pithed rats. In control, saline-treated pithed rats, resting plasma DA was found to be high, at around 9,000 pg/ml (8750±217 pg/ml), higher than any other CA. Remarkably, all 3 isomers of mecamylamine markedly lowered basal plasma DA levels to around 500 pg/ml±104 ($p<0.001$). In spite of markedly reduced baseline DA levels after the injections of the drugs, the sympathetic stimulation at 2.2 Hz still caused significant increases in plasma DA levels in saline-exo-R-mecamylamine- and the racemate-treated rats, but not in rats treated with exo-S-mecamylamine. In both, R318- and R319-treated rats, stimulation-induced increases in plasma DA were significantly lower than in saline-treated rats.

The present study demonstrated that mecamylamine has profound effects on cardiovascular and CA responses to sympathetic nerve stimulation in vivo in pithed rats. All three forms of mecamylamine were effective in reducing pressor, tachycardic and CA responses to sympathetic nerve stimulation but with some slight differences. All three forms had similar effects on the pressor and tachycardic responses to nerve stimulation, significantly lowering them at the higher frequencies of stimulation, as compared to those of the control, vehicle-treated rats. Yet, of the three, exo-S-mecamylamine was the most potent in decreasing stimulation-induced pressor responses (already at the lowest dose of 0.1 mg/kg). Exo-S-mecamylamine was also the only one that significantly decreased stimulation-evoked plasma NE increases. As far as plasma EPI responses are concerned, both exo-R-mecamylamine and the racemate significantly decreased them as compared to the control responses. And finally, all three isomers lowered the elevated resting plasma DA levels in the pithed rats but only the stereoisomers (not the racemate) reduced the stimulation-induced DA responses. Overall, exo-S-mecamylamine was the most effective in reducing plasma CA as well as decreasing sympathetically-mediated cardiovascular responses.

These results suggest that mecamylamine may exert receptor- and non-receptor mediated effects at the peripheral sympathetic neuro-effector junctions, through exo-R-mecamylamine and S-stereoisomers. The lowering effects of mecamylamine on the stimulation-evoked plasma NE and EPI levels, and on pressor and tachycardic responses, are consistent with its receptor-mediated presynaptic actions at both the peripheral sympathetic nerves and the adrenal medulla.

In conclusion, mecamylamine inhibits sympathetically mediated pressor, tachycardic and adrenergic (NE, EPT, DA) responses possibly by reducing the release of those neurotransmitters at the peripheral neuroeffector junctions and the chromaffin cells of the adrenal medulla. However, the major hypotensive effect of mecamylamine appears to be not stereoisomer-specific and may be related to reduction of high circulating DA levels, present in the pithed rats.

EXAMPLE 4

This experiment evaluated the efficacy and potency of exo-S-mecamylamine on human $\alpha_3\beta_4$, $\alpha_4\beta_2$, $\alpha_3\beta_2$, and $\alpha_7$ receptors expressed in Xenopus oocytes and compared its activity to that of mecamylamine racemate. Voltage dependence and binding reversibility also were determined. Mature female Xenopus laevis African toads were used as a source of oocytes. After linearization and purification of cloned cDNAs, RNA transcripts were prepared in vitro using the appropriate mMessage mMachine® kit from Ambion Inc. (Austin Tex.). Harvested oocytes were treated with collagenase (Worthington Biochemical Corporation, Freehold N.J.) for two hr at room temperature in calcium-free solution. Subsequently stage 5 oocytes were isolated and injected with 50 nL each of a mixture of the appropriate subunit(s) cRNAs. Recordings were made about 1-7 days after cRNA injection.

For electrophysiology, oocyte recordings were made with an oocyte amplifier (e.g., Warner Instruments, Hamden, Conn., No. OC-725C) and RC-8 recording chamber. Oocytes were placed in the recording chamber with a total volume of about 0.6 ml and perfused at room temperature by frog Ringer's solution (115 mM NaCl, 2.5 mM KCl, 10 mM HEPES pH 7.3, and 1.8 mM $CaCl_2$) containing 1 .mu.M atropine to inhibit potential muscarinic responses. A Mariotte flask filled with Ringer's solution was used to maintain a constant hydrostatic pressure for drug delivery and washes. Drugs were diluted in perfusion solution and loaded into a 2 ml loop at the terminus of the perfusion line. A bypass of the drug-loading loop allowed bath solution to flow continuously while the drug loop was loaded. The drug application was synchronized with data acquisition by using a 2-way electronic valve. The rate of bath solution exchange and drug application was preferably about 6 ml/min. Current electrodes were filled with a solution containing 250 mMCsCl, 250 mM CsF and 100 mM EGTA and had resistances of 0.5-2 M$\Omega$. Voltage electrodes were filed with 3M KCl and have resistances of 1-3M$\Omega$. Oocytes with resting membrane potentials more positive than −30 mV were not used.

Measurements of current responses to exo-S-mecamylamine application were studied under two-electrode voltage clamp at a holding potential of −50 mV unless otherwise noted. Holding currents immediately before agonist application were subtracted from measurements of the peak response to agonist. All drug applications were separated by at least a 5 min wash period, longer if there is persisting drug effect. At the start of recording, all oocytes received two initial control applications of acetylcholine (Ach). The second application of control ACh minimized the effects of rundown that occasionally occur after an initial ACh-evoked response. The second application of ACh also was used to normalize for the level of channel expression in each oocyte. To determine residual inhibitory effects, application of ACh with inhibitor or inhibitor alone was followed by another application of ACh alone and compared to the pre-application control ACh response.

For each receptor subtype, a control ACh concentration was selected that is sufficient to stimulate the receptors to a level representing a reasonably high value of $p_{open}$ at the peak of the response while minimizing rundown from successive ACh applications. Such conditions were adequate to achieve maximal inhibition. The control ACh concentration were 30 μm ACh for $\alpha_4\beta_2$, 100 μM ACh for $\alpha_3\beta_4$, 30 μM ACh for $\alpha_3\beta_2$, 300 μM ACh for $\alpha_7$, and 3 μM ACh for $\alpha_1\beta_1\delta\epsilon$. These correspond to the $EC_{30}$, $EC_{10}$, $EC_{15}$, $EC_{50}$, and $EC_{50}$, respectively, for these receptors.

For experiments assessing voltage-dependence of drug inhibition, oocytes were initially voltage clamped at a holding potential of −40 mV or −90 mV and 0.1 control application of ACh alone was delivered. A second control response was then obtained at the designated test potential. The holding potential was kept at the designated voltage for the co-application of ACh with exo-S-mecamylamine. Residual inhibition was evaluated with a subsequent application of ACh alone at the test potential, after a 5-min wash period.

Inhibition of $\alpha_3\beta_4$, $\alpha_4\beta_2$, $\alpha_3\beta_2$, and $\alpha_7$ receptors was tested with exo-S-mecamylamine. For each of the β subunit-containing receptor subtypes, there was a marked decrease in subsequent control response to ACh when it was applied 5 min after exposure to exo-S-mecamylamine. The residual inhibition was greatest for $\beta_2$-containing receptors and least for $\alpha_7$ receptors. Comparing the IC50 values, exo-S-mecamylamine was most potent at inhibiting $\alpha_3\beta4$ receptors and least potent at inhibiting $\alpha_7$ receptors.

The selectivity of mecamylamines for neuronal nAChR was tested by examining the effects of exo-S-mecamylamine on $\alpha_1\beta_1\delta\epsilon$ mouse muscle receptors. This isomer had very little effect; and after a 5-min wash, inhibition of muscle receptors was fully reversed, unlike the inhibition of β receptors. This decreased $\alpha_1\beta_1\delta\epsilon$ receptor effect indicates that exo-S-mecamylamine may cause less tiredness or weakness, which has been reported in smoking cessation studies and in a Tourette's study.

The effects of exo-S-mecamylamine also were tested on oocytes coexpressing NMDA receptor subunits NR1 and NR2b. NR1 is ubiquitous in the brain and produces robust functional responses when coexpressed with the NR2b subunit and activated by glutamate and the coagonist glycine. NR2b in vivo is selectively present in the forebrain with high levels of expression in the cerebral cortex and hippocampus, as well as the septum, caudate putamen and olfactory bulb, making the combination of NR2b and NR1 relevant for both cognitive and motor functions in the CNS. When exo-S- mecamylamine was applied to NR1/NR2b preparations at a concentration of 100 µM, it produced a transient inhibition to the co-application of 10 µM glutamate+10 µM glycine, which was reversible after a 5-min wash. These studies support the specific central nicotinic effect of exo-S-mecamylamine.

The recovery time course for nicotine receptors is important to note. Recovery time course experiments were performed at 5-min intervals and extended to about one-half hour. An initial inhibition of greater than 50% was obtained with the co-application of 10 µM exo-S-mecamylamine and ACh at the control concentration, and then followed the response recovery with control ACh applications every 5 min. For $\beta_2$ receptors, recovery from inhibition seemed to follow simple exponential kinetics. For $\alpha_3\beta_2$ receptors, exo-S-mecamylamine had a time constant of recovery of about 33 min, which was similar to the time constant of recovery of this isomer at $\alpha_4\beta_2$ receptors. Exo-S-mecamylamine off-loaded from some receptors slower than exo-R-mecamylamine which implies that a lower dosage or less frequent dosage may be used with the former. This could reduce toxicity.

In contrast to the $\beta_2$-containing receptors, recovery of $\alpha_3\beta_4$ receptors did not follow simple exponential kinetics. There appeared to be a fast phase lasting an average of 19 minutes. However, after that, there was no further recovery. This suggests that mecamylamine may exert two qualitatively different forms of inhibition on these receptors. Mecamylamine did not appear to compete with ACh on $\alpha_4\beta_2$ or $\alpha_4\beta_4$ receptors. The relative amount of inhibition produced by a fixed concentration of mecamylamine was relatively constant over a wide range of ACh concentrations. In the absence of ACh, mecamylamine at concentrations of 10 nM-100 µM were applied to receptors, but no agonist activity was observed.

The voltage dependence of the exo-S-mecamylamine activity was determined by co-applying ACh and isomer. First, cells were held at either −40 mV or 90 mV and tested for response to control concentrations of ACh. After a 5-min wash, ACh and the isomer were applied. This permitted the evaluation of voltage at the onset of inhibition and at recovery. Mecamylamine concentrations were 10 µM for $\alpha_7$ receptors, 5 µM for $\alpha_4\beta_2$ and $\alpha_3\beta_2$ receptors, and 1 µM for 60 $_3\beta_4$ receptors. There was significant voltage dependence for the $\alpha_4\beta_2$ and $\alpha_3\beta_4$ receptors. Exo-S-mecamylamine also had significantly different responses at $\alpha_3\beta_2$ and $\alpha_7$ receptors. These results indicate that the binding site for mecamylamine may be deep enough into the membrane's electric field to slow the dissociation of mecamylamine when the cell is hyperpolarized.

EXAMPLE 5

Cocaine use is an increasingly common problem in the United States, with estimates of lifetime use prevalence rates at 2.5% and current prevalence rates of cocaine abuse or dependence rates of about 1%. (Regier et al., 1990). There are no known effective treatments, aside from expensive, personnel-intensive supervision and counseling programs.

Many schizophrenic and depressed patients also have a high incidence of cocaine use; rates are estimated to be 40-50% (Shaner et al., 1995). Of cocaine abusers, it has been estimated that as many as 75% also are dependent on nicotine (Budney et al., 1993), as opposed to a smoking rate of 22% in controls.

Animal results with regard to cocaine, nicotine and mecamylamine have been equivocal. On the one hand, cocaine and its analogues bind calf brain with modest affinity to the non-competitive ion channel site on the high-affinity nAChR, the site of action of mecamylamine (Lerner-Marmarosh N, Carroll F I and Abood L G, Life Sciences 56(3):67-70, 1995). Cocaine was moderately effective in antagonizing the behavioral effects of nicotine. However, in mice, systemic administration of mecamylamine (1 mg/kg) and dihydro-beta-erythroidine (2 mg/kg)—nicotinic antagonists—and atropine (2 mg/kg)—a muscarinic antagonist—were ineffective against psychostimulant-induced stereotypy in naive animals. All three drugs were ineffective against either the induction or expression of cocaine sensitization. Karler, Brain Res. 1996 (July 1) 725(2):192-8. Spealman and Goldberg tested the effects of mecamylamine on the schedule-controlled behavior by intravenous injections of nicotine and cocaine in squirrel monkeys. J Pharm Exp Therap 223:403-06, 1982. Administering mecamylamine before the experimental session caused responding maintained by nicotine, but not by cocaine, to fall within saline-control levels.

This example utilizes HEK293 cells expressing cDNA for a variety of human neurotransmitters to determine a compound's affinity therewith and its ability to inhibit interactions with cocaine. The HEK 293 with inserts of hDAT (dopamine transporter), hSERT (serotonin transporter) or hNET (norepinephrine transporter) were grown to 80% confluence on 150 mm diameter tissue culture dishes and serve as the tissue source. Cell membranes were prepared as follows. Medium was poured off the plate, and the plate was washed with 10 ml of calcium- and magnesium-free phosphate-buffered saline. Lysis buffer (10 ml; 2 mM HEPES with 1 mM EDTA) was added. After 10 min, cells were scraped from plates, poured into centrifuge tubes, and centrifuged at 20,000×g for 20 min. The supernatant fluid was removed, and the pellet resuspended in 12-32 mil of 0.32 M sucrose using a Polytron centrifuge setting of 7 for 10 sec. The resuspension volume depends on the density of binding sites within a cell line and was chosen to reflect binding of 10% or less of the total radioactivity. Exo-S-mecamylamine was weighed and made up into a 10 mM stock solution in DMSO. Subsequent dilutions were made in assay buffer, achieving a final concentration of 0.1%.

For the assay, each tube was prepared with 50 µl of membrane preparation (about 10-15 µg of protein), 25 µl of ex-S-mecamylamine or buffer (Krebs-HEPES, pH 7.4; 122 mM NaCl, 2.5 mM CaCl$_2$, 1.2 mM MgSO4, 10 µm pargyline, 100 µM tropolone, 0.2% glucose and 0.02% ascorbic acid, buffered with 25 mM HEPES), 25 µl of [$^{125}$I]RTI-55 (40-80 pM final concentration) and additional buffer sufficient to bring up the final volume to 250 µl. Membranes were preincubated with exo-S-mecamylamine for 10 min prior to the addition of the [$^{125}$I]RTI-55. The assay tubes were incubated at 25° C. for 90 min. Binding was terminated by filtration over GF/C filters using a Tomtec 96-well cell harvester. Filters were washed for six seconds with ice-cold saline. Scintillation fluid was added to each square and radioactivity remaining on the filter was determined using a Wallac µ- or β-plate reader. Specific binding was defined as the difference in binding observed in the presence and absence of 5 µM mazindol (HEK-hDAT and HEK-hNET) or 5 µM imipramine (HEK-hSERT). Two or three independent competition experiments were conducted with duplicate determinations. GraphPAD Prism statistical program was used to analyze the resulting data, with IC50 values converted to Ki values using the Cheng-Prusoff equation.

The affinity of exo-S-mecamylamine for each type of binding site was lower than the affinity of cocaine for the same site.

EXAMPLE 6

The effect of exo-S-mecamylamine in cocaine addiction treatment was assessed in a locomotor depression test. The study was conducted using 40 Digiscan activity-testing chambers (40.5×40.5×30.5 cm) housed in sets of two, within sound-attenuating chambers. A panel of infrared beams (16 beams) and corresponding photodetectors were located in the horizontal direction along the sides of each activity chamber. A 7.5-W incandescent light above each chamber provided dim illumination. Fans provided an 80-dB ambient noise level within the chamber. Separate groups of 8 non-habituated male Swiss-Webster mice (Hsd:ND4, aged 2-3 months) were injected via the intraperitoneal (ip) route with either vehicle (0.9% saline) or exo-S-mecamylamine (0.3, 1.3, or 10 mg/kg doses), 20 minutes prior to locomotor activity testing. Just prior to placement in the apparatus, all mice received a saline injection. In all studies, horizontal activity (interruption of photocell beams) was measured for one hour within 10-min periods. Testing was conducted with one mouse per activity chamber.

First, saline and four doses of exo-S-mecamylamine were tested alone for 60 minutes. The exo-S-mecamylamine dose producing one half of the maximal depressant activity (where maximal depression is 0 counts in 30 minutes) was calculated as 8.5 mg/kg. Stimulant effects of 1 and 3 mg/kg doses were evident during the last 30 minutes of testing. Then the cocaine interaction study was performed as a function of time and exo-S-mecamylamine dose. Twenty minutes following injection of saline or mecamylamine, saline or 20 mg/kg cocaine ip was administered, and mice were placed in the Digiscan apparatus for one hour. Cocaine's effect is believed to be maximal at 30 minutes. At that time point, saline/cocaine was producing the highest locomotion; whereas, the administration of saline/saline and 10 mg/kg exo-S-macamylamine/cocaine were both significantly different from the result of cocaine alone. Interesting, the latter two test groups diverged by the end of the hour: The locomotion of the saline/saline group steadily declined to 60 minutes; whereas, the 10 mg/kg group's locomotion did not decrease further. The reported attenuated locomotor activity index ($AD_{50}$) was 3.3 mg/kg for exo-S-mecamylamine, compared to 6.2 mg/kg for exo-R-mecamylamine.

Other Uses

Recent reports suggest that nicotine reduces the symptoms of schizophrenia (Adler L E et al, Am J Psychiatry 150:1856-1861, 1993), Attention Deficit Hyperactivity Disorder (ADHD) (Levin E D et al, Psychopharmacology 123:55-62, 1995) and depression (Salin-Pascual R J et al, Psychopharmacology 121(4):476-479, 1995). While it is generally believed that nAChr activation is responsible for nicotine's therapeutic actions in these "nicotine-responsive" disorders (Decker M W et al, Life Sci, 56:545-570, 1995), it is clear that, like many other drugs, nicotine has complex neuropharmacological effects. Thus, many people with such nicotine-responsive disorders, could be helped with a nAChr blocker which has been disclosed herein with the example of mecamylamine, a nAChr blocker, which reduced the symptoms in the nicotine responsive disorders, TS and ADHD.

Schizophrenia, a psychiatric disorder theorized to involve hyperdopaminergic tone, is most often treated with neuroleptics; but there is now speculation that it is a nicotine-responsive disorder. For example, surveys of schizophrenic patients have demonstrated rates of smoking between 74% and 92%, compared to 35% to 54% for all psychiatric patients and 30%-35% for the general population. It has been speculated that cigarette smoking may improve underlying psychopathology by enhancing concentration and reducing anxiety from hyperarousal (Gopalaswamy A K, Morgan R, Br J Psychiatry, 149:523, 1986). In addition, nicotine may have some role to play in reducing the cognitive deficits associated with schizophrenia and neuroleptic treatment. Cigarette smoking has been found to normalize sensory gating deficits in schizophrenic patients (Adler L E et al, Am J Psychiatry 150:1856-1861, 1993) and a recent study found that transdermal nicotine reversed some of the adverse cognitive effects of standard antipsychotic medication and improved cognitive performance in general for schizophrenic patients (Levin E D et al, Psychopharmacology 123:55-63, 1996). If as we now hypothesize that nicotine administration may actually have a similar effect as a nAChr blocker, then it is possible that a nAChr blocker such as a mecamylamine isomer would also reverse the adverse cognitive effects of the antipsychotic medication and improve cognitive performance in schizophrenic patients. Moreover, since nicotine potentiates the therapeutic effects of neuroleptics in TS (McConville B J et al, Biological Psychiatry 31: 832-840, 1992), the use of mecamylamine as an adjunct to neuroleptics in "neuroleptic-responsive" disorders such as schizophrenia and Huntington's chorea, can allow for reducing the neuroleptic dose, thereby reducing the side effects of the neuroleptic without reducing its therapeutic effects. Nevertheless, based on the above experiences of mecamylamine in Tourette's, bipolar patients and patients with schizophrenia-like symptoms, cocaine abusers are also likely to benefit from treatment with mecamylamine and other nicotine antagonists.

The treatment of viral infections, particularly herpes I and II, has been successfully undertaken with ganglionic blocking agents tetraethylammonium or hexamethonium (U.S. Pat. No. 5,686,448). Because exo-S-mecamylamine has ganglionic blocking action, it can be expected to be similarly efficacious against viral infections.

Mecamylamine has been shown to reduce organophosphate poisoning toxicity. For example, when rats were dosed with 8 mg/kg of DFP (an organophosphate), all died within 5 hours. However, 3 of 4 rats receiving mecamylamine at 30 mg/kg and the lethal dose of DFP survived beyond 5 hours. Rats receiving a combination of mecamylamine and 2-PAM and then the lethal dose of DFP all survived. It would be beneficial to lower the dose of mecamylamine by administering only the effective isomer.

$Alpha_4$, but not $alpha_3$ and $alpha_7$, nicotinic acetylcholine receptor subunits are lost from the temporal cortex in Alzheimer's disease. Neuronal nicotinic acetylcholine receptors labelled with tritiated agonists are reduced in the cerebral cortex in Alzheimer's disease (AD). Autopsy tissue from the temporal cortex of 14 AD cases and 15 age-matched control subjects were compared using immunoblotting with antibodies against recombinant peptides specific for $alpha_3$, $alpha_4$, and $alpha_7$ subunits, in conjunction with [$^3$H]epibatidine binding. Antibodies to $alpha_3$, $alpha_4$, and $alpha_7$ produced one major band on western blots at 59, 51, and 57 kDa, respectively. [$^3$H]Epibatidine binding and $alpha_4$-like immunoreactivity (using antibodies against the extracellular domain and cytoplasmic loop of the $alpha_4$ subunit) were reduced in AD cases compared with control subjects ($p<0.02$) and with a subgroup of control subjects (n=9) who did not smoke prior to death ($p<0.05$) for the former two parameters. [$^3$H]Epibatidine binding and cytoplasmic alpha$_4$-like immunoreactivity were significantly elevated in a subgroup of control subjects (n=4) who had smoked prior to death (p<0.05). There were no significant changes in alpha$_3$- or alpha$_7$-like immunoreactivity associated with AD or tobacco use. The selective involvement of alpha$_4$ has implications for understanding the role of nicotinic receptors in AD and potential therapeutic targets (Martin-Ruiz C M et al. Neurochem 1999 October; 73(4):1635-40).

Cancer also may be treated with mecamylamines. Lung cancer demonstrates a strong etiologic association with smoking. Of the two most common histologic lung cancer types, small cell carcinoma (SCLC) is found almost exclusively in smokers, whereas peripheral adenocarcinoma (PAC) also develops in a significant number of nonsmokers. N'-Nitrosonornicotine (NNN) and 4(methylnitrosamino)-1-(3-pyridyl)-1-buta- none (NNK), nicotine-derived nitrosamines, are potent lung carcinogens contained in tobacco products (Schuller & Orloff, 1998).

Using cell lines derived from human small cell lung carcinoma and pulmonary adenocarcinoma with the nicotinic receptor selective ligands alpha-bungarotoxin (alpha-BTX) and epibatidine (EB) in receptor binding and cell proliferation assays, it was reported that SCLC expressed neuronal nicotinic receptors with high affinity to alpha-BTX, whereas PAC cells expressed nicotinic receptors with high affinity to EB (Schuller & Orloff, Biochem Pharmacol 55(9):1377-84, 1998). NNK bound with high affinity to alpha-BTX-sensitive nAChRs in SCLC cells, while NNN bound with high affinity to EB sensitive nAChRs in PAC cells. The affinity of each nitrosamine to these receptors was several orders of magnitude greater than that of nicotine. NNK stimulated the proliferation of SCLC cells via this mechanism. These findings suggest that NNK may contribute to the genesis of SCLC in smokers via chronic stimulation of the alpha BTX-sensitive nAChR-subtype expressed in these cells, which is most likely the alpha$_7$ containing subunit (Schuller et al., 2000). The alpha$_7$ nicotinic acetylcholine receptor and its associated mitogenic signal transduction pathway is emerging as an important growth regulator of pulmonary neuroendocrine cells and small cell lung carcinoma and may be critically involved in the development of neoplastic and non-neoplastic pulmonary diseases.

Mecamylamine, especially the exo-S-mecamylamine, would be expected to interrupt nicotine and NNK stimulated the proliferation of SCLC cells in smokers and thus should be useful for treating SCLC.

The foregoing description and examples are intended only to illustrate, not limit, the disclosed invention.

All of the patents, patent applications and references referred to above are incorporated herein by reference.

We claim:

1. A method of treating a medical condition selected from the group consisting of substance addiction, Tourette's Syndrome, a neuropsychiatric disorder, depression, and anxiety, in a human in need thereof, comprising orally administering a therapeutically effective amount of a pharmaceutical composition to the human, wherein the pharmaceutical composition comprises:
   exo-S-mecamylamine or pharmaceutically acceptable salt thereof substantially free of exo-R-mecamylamine or a pharmaceutically acceptable salt thereof,
   one or more pharmaceutically acceptable carriers; and
   a pharmaceutical adjuvant, wherein the pharmaceutical composition has a higher overall therapeutic index than the same amount of exo-R-mecamylamine substantially free of exo-S-mecamylamine.

2. The method of claim 1, wherein the pharmaceutical composition is a unit dosage form.

3. The method of claim 2, wherein the unit dosage form is selected from the group consisting of a tablet, capsule, soft gelatin capsule, hard gelatin capsule, powder, lozenge, gum, emulsion, suspension, syrup, and solution.

4. The method of claim 1, wherein the pharmaceutical composition is formulated to provide rapid, sustained, or delayed release of the exo-S-mecamylamine or a pharmaceutically acceptable salt thereof.

5. The method of claim 1, wherein the effective amount of exo-S-mecamylamine or pharmaceutically acceptable salt thereof is from about 0.001 mg/kg to about 6 mg/kg per day.

6. The method of claim 1, wherein the effective amount of exo-S-mecamylamine or pharmaceutically acceptable salt thereof is from about 0.01 mg/kg to about 1.5 mg/kg per day.

7. The method of claim 1, wherein the medical condition is substance addiction.

8. The method of claim 1, wherein the medical condition is Tourette's Syndrome.

9. The method of claim 1, wherein the medical condition is a neuropsychiatric disorder.

10. The method of claim 1, wherein the medical condition is depression.

11. The method of claim 1, wherein the medical condition is anxiety.

* * * * *